United States Patent
Scherzer et al.

(10) Patent No.: US 6,229,043 B1
(45) Date of Patent: May 8, 2001

(54) PREPARATION OF MIXTURES OF DIPHENYLMETHANE DIISOCYANATES AND POLYPHENYLPOLYMETHYLENE POLYISOCYANATES HAVING A REDUCED IODINE COLOR NUMBER AND A REDUCED CHLORINE CONTENT

(75) Inventors: Dietrich Scherzer, Neustadt; Bernd Bruchmann, Ludwigshafen; Roland Minges, Grünstadt; Peter Keller, Hirschberg; Willy van Pee, Kappellen; Wolfgang Heider, Neustadt; Siegmund Pohl, Ludwigshafen; Bernhard Otto, Limburgerhof; Paul Jacobs, Gravenwezel; Wilfried Seyfert, Weisenheim, all of (DE)

(73) Assignee: BASF Corporation, Mt. Olive, NJ (US)

( * ) Notice: Subject to any disclaimer, the term of this patent is extended or adjusted under 35 U.S.C. 154(b) by 0 days.

(21) Appl. No.: 08/675,428

(22) Filed: Jun. 26, 1996

(30) Foreign Application Priority Data

Jun. 30, 1995 (DE) .............................................. 195 23 851

(51) Int. Cl.$^7$ .................................................. C07C 249/14
(52) U.S. Cl. ........................ 560/333; 560/347; 560/352
(58) Field of Search ................................... 560/333, 347, 560/352

(56) References Cited

U.S. PATENT DOCUMENTS

| | | |
|---|---|---|
| 2,885,420 | 5/1959 | Spiegler . |
| 4,465,639 | 8/1984 | Hatfield, Jr. . |
| 4,677,221 | 6/1987 | Müller et al. . |
| 5,207,942 | * 5/1993 | Scherzer et al. .................. 252/182.2 |
| 5,208,368 | * 5/1993 | Scherzer et al. ..................... 560/333 |

FOREIGN PATENT DOCUMENTS

| | | |
|---|---|---|
| 770026 | 10/1967 | (CA) . |
| 0 445 602 A2 | 2/1991 | (EP) . |
| 0 467125 | 6/1991 | (EP) . |
| 467125 | 1/1992 | (EP) . |
| 1097219 | 1/1968 | (GB) . |
| 1465014 | 2/1977 | (GB) . |

* cited by examiner

*Primary Examiner*—Samuel Barts
(74) *Attorney, Agent, or Firm*—Fernando A. Borrego; Mary A. Golota

(57) ABSTRACT

Mixtures of diphenylmethane diisocyanates and polyphenylpolymethylene polyisocyanates (raw MDI) having a reduced iodine color number and a reduced chlorine content are prepared by reacting the corresponding mixtures of diphenylmethanediamines and polyphenylpolymethylenepolyamines with phosgene in the presence of at least one inert organic solvent at elevated temperature, and then, after phosgenation is complete, incorporating into the reaction mixture, in the presence or absence of the phosgene, a mixture of water and at least one monohydric or polyhydric polyoxyalkylene alcohol, preferably having a functionality of from 2 to 3, and advantageously having a hydroxyl number of from 20 to 1800, in an effective amount which advantageously comprises from more than 0.01 to 0.3% by weight of water (i) and from 0.5 to 5% by weight of a polyoxyalkylene alcohol (ii), in each case based on the weight of raw MDI, then removing the excess phosgene or the phosgene residues still present and the inert organic solvent, if desired adding to the reaction product up to 5% by weight, based on the weight of raw MDI, of at least one antioxidant based on phenol and/or aryl phosphite and thermally treating the reaction mixture.

19 Claims, No Drawings

PREPARATION OF MIXTURES OF DIPHENYLMETHANE DIISOCYANATES AND POLYPHENYLPOLYMETHYLENE POLYISOCYANATES HAVING A REDUCED IODINE COLOR NUMBER AND A REDUCED CHLORINE CONTENT

BACKGROUND OF THE INVENTION

1. Field of the Invention

The present invention relates to a process for preparing mixtures of diphenylmethane diisocyanates and polyphenylpolymethylene polyisocyanates known as raw MDI, having a reduced iodine color number and a reduced chlorine content by reacting the corresponding mixtures of diphenylmethanediamines and polyphenylpolymethylenepolyamines, known as raw MDA, with phosgene in the presence of at least one inert organic solvent, wherein a mixture of water and at least one monohydric or polyhydric polyoxyalkylene alcohol in an effective amount is incorporated into the reaction mixture after phosgenation is complete.

Raw MDI, one of the industrially most important starting materials for preparing polyisocyanate polyaddition products, for example urethane foams or foams containing urethane and isocyanurate groups, and for preparing diphenylmethane 4,4'-diisocyanate, an important formative component for producing polyurethane (PU) elastomers, or fibers, sealing compounds, adhesives, etc. is prepared in a known manner by reaction of raw MDA with phosgene, customarily in the presence of an inert organic solvent. Raw MDA is in turn obtained by condensation of aniline and formaldehyde in the presence of acid catalysts, with the percentages of diphenylmethanediamines and the homologous polyphenylpolymethylenepolyamines and their isomers being able to be controlled as a function of the mixing ratios selected for the starting materials and of the reaction conditions and the various processes (Kunststoff-Handbuch, Volume 7, Polyurethane, 1st Edition 1966 and 2nd Edition 1983, Carl-Hanser-Verlag, Munich, Vienna). If the condensation of aniline and formaldehyde is, for example, carried out in the presence of weakly acid catalysts, the raw MDA mixtures obtained have a relatively high proportion of 2,2'- and 2,4'-diaminodiphenylmethanes, while raw MDA mixtures having a high content of 4,4'-diaminodiphenylmethane and at the same time a low proportion of 2,4'-diaminodiphenylmethane can be prepared only in the presence of relatively large amounts of strongly acid catalysts, preferably strong mineral acids such as hydrochloric acid.

The ratio of the diaminodiphenylmethane isomers to the higher homologs in raw MDA is also dependent on the aniline/formaldehyde ratio and the condensation temperature, with larger aniline/formaldehyde ratios and low condensation temperatures giving high diaminodiphenylmethane contents (CA-A-770 026).

A disadvantage of these preparative processes which are described in many literature and patent publications is the formation of more or less strongly colored raw MDA whose color can vary from black through darker and paler brown shades to ochre. A further disadvantage is that these discolorations are not, or only insufficiently, reduced by the subsequent reaction with phosgene for preparing the corresponding raw MDI and the raw MDI formed cannot be purified by distillation. Furthermore, this undesired discoloration affects the downstream products, so that the polyisocyanate polyaddition products, which may be cell-containing, produced from colored raw MDI are also not colorless. Although the intrinsic color of the polyisocyanate polyaddition products does not adversely affect their mechanical properties, essentially colorless products are desired by the consumer.

There have therefore been many attempts to reduce the discoloration of raw MDI and to stabilize the polyisocyanates produced by means of suitable process measures or additives.

According to U.S. Pat. No. 2,885,420, organic polyisocyanates can be stabilized against discoloration by the addition of from 0.01 to 0.5% by weight, based on the weight of polyisocyanate, of an aromatic, cycloaliphatic or aliphatic ether or thioether.

To eliminate impurities which act as gel-formation catalysts in organic diisocyanate solutions, from about 0.001 to 1% by weight, based on the weight of the diisocyanate, of phosphoric acid is, according to DE-A-1 280 855 (GB 1 097 219), added to the solutions.

GB-B-1 465 014 describes the addition of glycidol in an amount of from 0.001 to 0.25% by weight, based on the weight of diisocyanate, for improving the storage stability of distilled diphenylmethane diisocyanates.

EP-B-0 183 976 (U.S. Pat. No. 4,677,221) relates to a process for preparing thermally color-stable (cyclo)aliphatic diisocyanates, in which process technical-grade diisocyanate is heated with aliphatically and/or cycloaliphatically bonded isocyanate groups in the presence of from 0.1 to 3% by weight of a compound soluble in the diisocyanate, which compound contains at least 3% by weight of structural units of the formula —NH—CO—, at from 100 to 220° C. for a period of up to 5 hours and the diisocyanate thus treated is subsequently purified by distillation. The process cannot be applied to the treatment of raw MDI since, as already indicated, this is not distillable.

According to U.S. Pat. No. 4,465,639, raw MDI has incorporated into it, after phosgenation is complete but before complete removal of the phosgene, from 0.1 to 5% by weight of water, based on the polyisocyanate weight in the reaction mixture. The color of the raw MDI and the PU foams produced therefrom can be lightened by this measure. Furthermore, the proportion of higher molecular weight MDI homologs in the raw MDI is considerably lowered and their viscosity is reduced. Although the iodine color number of the raw MDI can be lowered in this manner, this method is also associated with considerable disadvantages. The presence of water considerably increases the corrosive action of the reaction mixture containing chlorine, hydrogen chloride and phosgene on the equipment of the production plant and thereby increases the risk of leakage, associated with an escape of toxic phosgene or a phosgene-containing reaction mixture. For safety reasons, prevailing opinion is therefore that moisture in any form should be essentially completely excluded in phosgenation.

According to EP-A-0 467 125, the iodine number of raw MDI can be reduced by incorporating an effective amount of monohydric or polyhydric polyoxyalkylene alcohols or mixtures thereof in place of water into the reaction mixture after completion of phosgenation. Although this process enables the iodine color number of the raw MDI to be considerably reduced, for example to values of less than 60, preferably from 35 to 20, this method too has dis- advantages. A disadvantage is, for example, that the addition of the polyoxyalkylene alcohols reduces the isocyanate content of the raw MDI and the chlorine content, particularly the total chlorine content, rises and the viscosity can increase with increasing storage time.

DETAILED DESCRIPTION OF THE INVENTION

It is an object of the present invention to reduce the abovementioned disadvantages to a minimum and to prepare storage-stable raw MDI having as high as possible an isocyanate content, as low as possible a total chlorine content and as low as possible an iodine color number.

We have found that this object is achieved by addition of a mixture of water and at least one monohydric and/or polyhydric polyoxyalkylene alcohol to the phosgene-containing or advantageously predominantly phosgene-free reaction mixture containing raw MDI after phosgenation is complete.

The present invention accordingly provides a process for preparing raw MDI having a decreased iodine color number and a reduced chlorine content by reacting the corresponding raw MDA with phosgene in the presence of at least one inert organic solvent at elevated temperature, separating off the excess phosgene and solvent after phosgenation and thermally treating the reaction product obtained, wherein a mixture comprising or preferably consisting of water and at least one monohydric or polyhydric polyoxyalkylene alcohol or mixture thereof is incorporated in an effective amount into the reaction mixture after phosgenation is complete, in the presence or absence of the phosgene.

Surprisingly, the process of the present invention enables the preparation of raw MDI having an iodine color number which is lower than that obtained when water alone is used as additive and corresponds approximately to the iodine color number level which can be achieved with sole use of polyoxyalkylene alcohols or mixtures thereof. Furthermore, it was surprising that the addition according to the present invention of a mixture of water and at least one polyoxyalkylene alcohol increases the isocyanate content of the raw MDI in comparison with sole use of at least one polyoxyalkylene alcohol and reduces the content of easily hydrolyzable and difficult-to-hydrolyze chlorine and also, in particular, the total chlorine content. This synergistic effect was as unforeseeable as the suppression of the corrosive action of the reaction mixture containing chlorine, hydrogen chloride and phosgene on the steel equipment of the production plant in the presence of the added amounts of water and polyoxyalkylene alcohols required according to the present invention.

The mixtures of diphenylmethane diisocyanates (MDI) and polyphenylpolymethylene polyisocyanates prepared by the process of the present invention preferably have an MDI isomer content of from 30 to 90% by weight, preferably from 30 to 70% by weight, an isocyanate content of from 30 to 33% by weight, preferably from 30.5 to 32.5% by weight, in each case based on the weight of raw MDI, an iodine color number of from 20 to 60, preferably from 25 to 40, a content of easily hydrolyzable chlorine of from 100 to 300 ppm, preferably from 120 to 200 ppm, of difficult-to-hydrolyze chlorine of from 500 to 2000 ppm, preferably from 800 to 1400 ppm, a total chlorine content of from 1500 to 4000 ppm, preferably from 1700 to 3000 ppm, and a viscosity of at most 2000 mpa.s, preferably from 40 to 350 mpa.s, measured at 25° C. in accordance with DIN 53 019.

Raw MDIs having such isomer and homologous compositions can, as already indicated, be prepared by phosgenation of raw MDAs having corresponding product compositions in the presence of at least one inert organic solvent by known methods.

Suitable raw MDAs are advantageously obtained by condensation of aniline and formaldehyde in a molar ratio of 6–1.6:1, preferably 3–1.9:1, and a molar ratio of aniline to acid catalysts of 1:0.98–0.01, preferably 1:0.8–0.2.

The formaldehyde is preferably used in the form of an aqueous solution, eg. as a commercial 30–50% strength by weight solution.

Acid catalysts which have been found to be useful are proton donors such as acid ion-exchange resins or strong organic and preferably inorganic acids. For the purposes of the present invention, strong acids are those having a pKs of less than 1.5; in the case of polybasic acids this value is that for the first hydrogen dissociation step. Examples which may be mentioned are hydrochloric acid, sulfuric acid, phosphoric acid, fluorosulfonic acid and oxalic acid. Hydrogen chloride can also be used in gaseous form. Preference is given to using aqueous hydrochloric acid in concentrations from about 25 to 31% by weight.

Suitable processes for preparing raw MDA are described, for example, in CA-A-700 026, DE-B-22 27 110 (U.S. Pat. No. 4,025,557), DE-B-22 38 920 (U.S. Pat No. 3,996,283), DE-B-24 26 116 (GB-A-1 450 632), DE-A-12 42 623 (U.S. Pat. No. 3,478,099), GB-A-1 064 559 and DE-A-32 25 125.

The other starting component used for preparing raw MDI is phosgene. The gaseous phosgene can be used as such or diluted with gases which are inert under the reaction conditions, for example nitrogen, carbon monoxide, etc. The molar ratio of raw MDA to phosgene is advantageously such that from 1 to 10 mol, preferably from 1.3 to 4 mol, of phosgene are present in the reaction mixture per $NH_2$ groups.

Suitable inert organic solvents are compounds in which the raw MDA and the phosgene are at least partially soluble.

Solvents which have been found to be very useful are chlorinated, aromatic hydrocarbons, for example monochlorobenzene, dichlorobenzenes such as o-dichlorobenzene, p-dichlorobenzene, trichlorobenzenes, the corresponding toluenes and xylenes, chloroethylbenzene, monochlorobiphenyl, α- or β-naphthyl chloride and dialkyl phthalates such as diethyl isophthalate. Particularly useful inert solvents are monochlorobenzene, dichlorobenzenes or mixtures of these chlorobenzenes. The solvents can be used individually or as mixtures. The solvent used is advantageously one which has a lower boiling point than the MDI isomers so that the solvent can easily be removed from the raw MDI by distillation. The amount of solvent is advantageously such that the reaction mixture has a raw MDI content of from 2 to 40% by weight, preferably from 5 to 20% by weight, based on the total weight of the reaction mixture.

The raw MDA can be used as such or dissolved in organic solvents. However, preference is given to using raw MDA solutions having a raw MDA content of from 2 to 40% by weight, preferably from 5 to 20% by weight, based on the total weight of the amine solution.

According to the present invention, the iodine color number is reduced by incorporating mixtures of water and at least one monohydric or polyhydric polyoxyalkylene alcohol or mixtures of monohydric, polyhydric or mono- and polyhydric polyoxyalkylene alcohols in an effective amount into the phosgene-containing reaction mixture.

The water used for this purpose can be, for example, drinking water. However, water free of metal ions, for example distilled water or water purified by means of an ion exchanger, is advantageously used.

Suitable monohydric and polyhydric polyoxyalkylene alcohols advantageously have a hydroxyl number of from 20 to 1800, preferably from 100 to 1100 and in particular from 200 to 800, and the polyhydric polyoxylene alcohols advantageously have a functionality of preferably from 2 to 8 and in particular from 2 to 3. Polyoxyalkylene alcohols which have been found to be very useful are ones which are, in the effective amounts required, at least partially, but preferably completely, soluble in the inert organic solvents for preparing the raw MDI, preferably monochlorobenzene, dichlorobenzenes or mixtures thereof.

The polyoxyalkylene alcohols can be prepared by known methods, for example by anionic polymerization using alkali metal hydroxides such as sodium or potassium hydroxide or alkali metal alkoxides such as sodium methoxide, sodium or potassium ethoxide or potassium isopropoxide as catalysts and with addition of at least one initiator molecule containing at least one, preferably from 2 to 8 and in particular 2 or 3, reactive hydrogens in bonded form, or by cationic polymerization using Lewis acids such as antimony pentachloride, boron trifluoride etherate, etc, or bleaching earth as catalysts, from one or more alkylene oxides having from 2 to 4 carbon atoms in the alkylene radical.

Suitable alkylene oxides are, for example, tetrahydrofuran, 1,3-propylene oxide, 1,2- or 2,3-butylene oxide, styrene oxide and preferably ethylene oxide and 1,2-propylene oxide. The alkylene oxides can be used individually, alternately in succession or as mixtures. Suitable initiator molecules are, for example: alkanols having branched or preferably linear alkyl radicals having from 1 to 10, preferably from 1 to 4, carbon atoms, for example methanol, ethanol, n- and iso-propanol, n- and sec-butanol, pentanol, hexanol, n- and iso-octanols, polyhydric, preferably dihydric to octahydric, in particular dihydric and/or trihydric, alcohols or alkylene glycols such as ethanediol, 1,2- and 1,3-propanediol, 1,4-butanediol, 1,5-pentanediol, 1,6-hexanediol, glycerol, trimethylolpropane, pentaerythritol, sorbitol and sucrose, and also diethylene glycol, dipropylene glycol and water.

Examples of suitable monohydric or polyhydric polyoxyalkylene alcohols are: polyoxytetramethylene, polyoxytetramethylene-polyoxypropylene, polyoxytetramethylene-polyoxyethylene, polyoxypropylene, polyoxypropylene-polyoxyethylene and polyoxyethylene alcohols. However, polyoxyalkylene alcohols which have been found to be particularly useful and are therefore preferably used are polyhydric polyoxyalkylene alcohols having a functionality of from 2 to 3 and a hydroxyl number of from 200 to 800, in particular from 240 to 600, advantageously those prepared from ethylene oxide, 1,2-propylene oxide or 1,2-propylene oxide and ethylene oxide, with the polyoxypropylene-polyoxyethylene alcohols obtained being able to contain the ethylene oxide and 1,2-propylene oxide units in bonded form randomly distributed or blockwise or randomly distributed with ethylene oxide end blocks. The monohydric or polyhydric polyoxyalkylene alcohols can be used individually or in the form of mixtures. Of course, mixtures of monohydric and polyhydric polyoxyalkylene alcohols are also suitable.

The amount of water and monohydric or/and polyhydric polyoxyalkylene alcohols in the mixture required to reduce the iodine color number and the chlorine content is dependent on the color or amount of impurities, which can comprise one or more unknown substances, in the raw MDI and the hydroxyl number of the polyoxyalkylene alcohols and can be experimentally determined by simple tests.

Good results are usually obtained when using from more than 0.01 to 0.3% by weight, preferably from more than 0.01% by weight to less than 0.1% by weight, of water, based on the weight of the raw MDI in the reaction mixture, and from 0.05 to 5% by weight, based on the weight of the raw MDI in the reaction mixture, of at least one polyoxyalkylene alcohol, with polyoxyalkylene alcohols having a hydroxyl number of less than 380 being advantageously used in an amount of from 0.1 to 5% by weight, in particular from 0.2 to 3% by weight, those having a hydroxyl number of from 200 to 800 being advantageously used in an amount of from 0.1 to 3% by weight, in particular from 0.2 to 1.5% by weight, and polyoxyalkylene alcohols having a hydroxyl number of greater than 800 being advantageously used in an amount of from 0.05 to 1.5% by weight, in particular from 0.1 to 1.0% by weight, in each case based on the weight of the solvent-free raw MDI.

The polyoxyalkylene alcohols can be used in pure or commercial quality. However, polyoxyalkylene alcohols having water contents higher than the usual commercial water contents are also suitable as long as the water content in the amount of polyoxyalkylene alcohol added does not exceed the amount of water required according to the present invention. When using such polyoxyalkylene alcohols having an increased water content it may be possible to omit separate addition of extra water, depending on the water content of the polyoxyalkylene alcohol.

After removing the phosgene and the inert solvent, it is possible to add, if desired, at least one antioxidant based on phenol, at least one aryl phosphite or a mixture of these stabilizers to the raw MDI containing water and monohydric and/or polyhydric polyoxyalkylene alcohols and/or reaction products obtainable from water and these monohydric and/or polyhydric polyoxyalkylene alcohols and raw MDI. If use is made of these stabilizers, which in association with the mixtures of water and polyoxyalkylene alcohols used according to the present invention can effect an additional reduction of the iodine color number, they are advantageously used in an amount of from 0 to at most 5% by weight, preferably from 0.01 to 3% by weight and in particular from 0.1 to 1.0% by weight, based on the weight of the raw MDI.

Examples of suitable antioxidants based on phenol are: styrenized phenols, ie. phenols containing a bonded 1-phenylethyl group in the 2 or 4 position or in the 2 and 4 and/or 6 position, bis[2-hydroxy-5-methyl-3-tert-butylphenyl]methane, 2,2-bis-[4-hydroxyphenyl]propane, 4,4'-dihydroxybiphenyl, 3,3'-dialkylor 3,3',5,5'-tetraalkyl-4,4'-dihydroxybiphenyl, bis[4-hydroxy-2-methyl-5-tert-butylphenyl] sulfide, hydroquinone, 4-methoxyphenol, 4-tert-butoxyphenol or 4-benzyloxyphenol, mixtures of 4-methoxy-2- or -3-tert-butylphenol, 2,5-di-hydroxy-1-tert-butylbenzene, 2,5-dihydroxy-1,4-di-tert-butylbenzene, 4-methoxy-2,6-di-tert-butyophenol and preferably 2,6-di-tert-butyl-p-cresol.

Aryl phosphites which have been found to be useful are tri(alkylphenyl) phosphites having from 1 to 10 carbon atoms in the alkyl radical, for example tri(methylphenyl), tri(ethylphenyl), tri(n-propylphenyl), tri(isopropylphenyl), tri(n-butylphenyl), tri(sec-butyphenyl), tri(tert-butylphenyl), tri(pentylphenyl), tri(hexylphenyl), tri(2-ethylhexylphenyl), tri(octylphenyl), tri(2-ethyloctylphenyl), tri(decylphenyl) phosphite and preferably tri(nonylphenyl) phosphate, and in particular triphenyl phosphite.

To prepare the raw MDIs having a reduced iodine color number and a reduced chlorine content by the process of the present invention, the corresponding raw MDAs are phosgenated, advantageously at a temperature in the range from 90 to 220° C., preferably front 120 to 180° C., at atmospheric pressure or preferably under super-atmospheric pressure, eg. at from 1 to 10 bar, preferably from 2 to 5 bar. The temperature used in the process of the present invention is above the decomposition temperature of the carbamic acid chlorides formed as intermediates by the reaction of raw MDA with phosgene. An increase in the pressure is limited only by technical and possibly safety considerations, but a greater increase in pressure no longer gives increases in yield.

After phosgenation is complete, the mixture of water and at least one monohydric and/or preferably polyhydric polyoxyalkylene alcohol, in particular a mixture of water and polyoxypropylene polyol or water-containing polyoxyalkylene alcohols or water-containing polyoxyalkylene alcohol mixtures can be added to the reaction mixture, which contains at least one inert organic solvent, dissolved raw MDI, excess phosgene, hydrogen chloride and by-products of the phosgenation, at, for example, from 20 to 220° C., preferably from 90 to 200° C. and in particular from 125 to 165° C. According to another process variant which is preferably used, after phosgenation is complete the excess phosgene is first almost completely removed from the reaction mixture. Subsequently, the appropriate mixture according to the present invention of water and at least one polyoxyalkylene alcohol is incorporated in an effective amount at a temperature in the abovementioned range into the reaction mixture which consists essentially of at least one inert organic solvent, dissolved raw MDI, phosgene residues which have not been removed, hydrogen chloride and by-products of the phosgenation. After a residence time of, for example, from 0.1 to 45 minutes, preferably from 2 to 25 minutes, at from 20 to 180° C., preferably from 70 to 180° C., the excess phosgene or, according to the preferred procedure, the phosgene residues still present can be removed essentially completely at atmospheric pressure and subsequently the inert organic solvent or mixture thereof can be removed essentially completely at from 30 to 180° C., preferably from 50 to 180° C., under reduced pressure, eg. at from 0.01 to 100 mbar, preferably from 0.1 to 50 mbar, preferably by distillation.

If it appears to be useful, at least one antioxidant based on phenol and/or at least one aryl phosphite can then be added in an effective amount to the raw MDIs containing water and monohydric and/or preferably polyhydric polyoxyalkylene alcohols and/or, in particular, reaction products of raw MDI with water and these polyoxyalkylene alcohols. The raw MDIs treated in this manner are then dechlorinated by heating to, for example, from 100 to 250° C., preferably from 140 to 200° C., and treated at this temperature under a pressure of, for example, from 0.01 to 100 mbar, preferably from 0.1 to 20 mbar, for at least 5 minutes and, in particular, from 5 to 45 minutes. After cooling to 60° C., the raw MDI is transferred to intermediate storage and is there allowed to cool further.

The raw MDIs prepared by the process of the present invention have a significantly reduced iodine color number, usually of at most 40, and are used for producing compact or foamed polyisocyanate polyaddition products, preferably flexible, semirigid or rigid foams containing urethane groups or urethane and isocyanurate groups, these foams having a significantly lighter color.

EXAMPLES

Example 1 and Comparative Examples I to IV

Water, a polyoxypropylene glycol having a hydroxyl number of 250 or a mixture according to the present invention of water and the specified polyoxypropylene glycol was added, at from 130 to 140° C. to a reaction mixture consisting of 90 parts by weight of monochlorobenzene as solvent,
a maximum of 1 part by weight of phosgene and raw MDI which in turn contained:
54.7% by weight of 4,4'-MDI,
2.4% by weight of 2,4'-MDI,
a maximum of 1% by weight of 2,2'-MDI and homologs containing more than two isocyanate groups and also unidentified by-products, with the parts by weight adding up to 100 parts by weight and the percentages by weight adding up to 100% by weight.

The reaction mixture was held for 5 minutes at from 130 to 140° C., subsequently heated to 175° C. over a period of about 20 minutes and the residual phosgene and the monochlorobenzene were distilled off at this temperature under reduced pressure (about 60 mbar).

The raw MDI obtained was then dechlorinated for 30 minutes at from 170 to 180° C. and under a reduced pressure of less than 10 mbar.

The raw MDI had a viscosity of 200 mpa.s at 25° C., measured in accordance with DIN 53 019, and the iodine color number (ICN), the total chlorine content (TC) and the isocyanate content were measured, with the raw MDI being diluted with monochlorobenzene in a volume ratio of 1:5 for determining the iodine color number in accordance with DIN 6162.

The amount of water and polyoxypropylene glycol used and the iodine color number, the total chlorine content TC and the isocyanate content determined on the raw MDI are summarized in Table 1.

TABLE 1

| Comparative Example | Polyoxypropylene glycol [% by weight, based on raw MDI] | Water [% by weight, based on raw MDI] | Raw MDI | | |
|---|---|---|---|---|---|
| | | | ICN [1:5] | TC [ppm] | Isocyanate content [% by weight] |
| I | — | — | 80 | 1600 | 31.5 |
| II | — | 0.02 | 70 | 2000 | 31.3 |
| III | — | 0.07 | 30 | 2100 | 31.3 |
| IV | 0.4 | — | 30 | 2300 | 31.1 |
| Example 1 | 0.4 | 0.02 | 25 | 1900 | 31.5 |

Example 2 and Comparative Example V

A glycerol-initiated polyoxypropylene polyol having a hydroxyl number of 560 or a mixture according to the present invention of water and the specified polyoxypropylene polyol was added at from 138 to 142° C. to a reaction mixture consisting of 90 parts by weight of monochlorobenzene as solvent,
a maximum of 1 part by weight of phosgene and raw MDI, which in turn contained:
55% by weight of 4,4'-MDI,
3.4% by weight of 2,4'-MDI,
a maximum of 1% by weight of 2,2'-MDI and homologs containing more than two isocyanate groups and also unidentified by-products, with the parts by weight adding up to 100 parts by weight and the percentages by weight adding up to 100% by weight.

The reaction mixture was held for 5 minutes at from 130 to 140° C., subsequently heated to 175° C. over a period of about 20 minutes and at this temperature the residual phosgene and the monochlorobenzene were distilled off under reduced pressure (about 60 mbar).

The raw MDI obtained was dechlorinated using a method similar to that in Example 1 and had a viscosity of 200 mpa.s. The iodine color number (ICN), the total chlorine content and the isocyanate content were measured, in each case based on the raw MDI weight.

The amount of water and polyoxypropylene polyol used and the analytical values determined are summarized in Table 2.

TABLE 2

| | | | Raw MDI | | |
|---|---|---|---|---|---|
| Comparative Example | Polyoxypropylene polyol [% by weight, based on raw MDI] | Water [% by weight, based on raw MDI] | ICN [1:5] | TC [ppm] | Isocyanate content [% by weight] |
| V | 0.4 | — | 70 | 3000 | 30.9 |
| Example 2 | 0.25 | 0.02 | 35 | 2700 | 31.3 |

We claim:

1. A process for preparing mixtures of diphenylmethane diisocyanates and polyphenylpolymethylene polyisocyanates having a reduced iodine color number and a reduced chlorine content by reacting the corresponding mixtures of diphenylmethanediamines and polyphenylpolymethylenepolyamines with phosgene in the presence of at least one inert organic solvent at elevated temperature, separating off the excess phosgene and solvent after phosgenation is complete and thermally treating time reaction product, wherein a mixture of water and at least one monohydric or polyhydric polyoxyalkylene alcohol or mixture thereof is incorporated in an effective amount into the reaction mixture after phosgenation is complete, in the presence or absence of the phosgene, said effective amount of said mixture comprising i) from more than 0.01 to 0.3% by weight of water and
   ii) from 0.05 to 5% by weight of at least one monohydric or polyhydric polyoxyalkylene alcohol,
   in each case based on the weight of the mixture of diphenylmethane diisocyanates and polyphenylpolymethylene polyisocyanates in the reaction mixture.

2. A process as claimed in claim 1, wherein the effective amount of the mixture comprises
   i) from more than 0.01 to less than 0.1% by weight of water and
   ii) from 0.05 to 5% by weight of at least one monohydric or polyhydric polyoxyalkylene alcohol,
   where the percentages by weight are in each case based on the 40 weight of the mixture of diphenylmethane diisocyanates and polyphenylpolymethylene polyisocyanates in the reaction mixture.

3. A process as claimed in claim 1, wherein the monohydric or polyhydric polyoxyalkylene alchols (ii) have a hydroxyl number of from 20 to 1800.

4. A process as claimed in claim 1, wherein the polyhydric polyoxyalkylene alcohols (ii) have a functionality of from 2 to 3 and a hydroxyl number of from 200 to 800.

5. A process as claimed in claim 1, wherein the monohydric or polyhydric polyoxyalkylene alcohols (II) are selected from the group consisting of polyoxyethylene, polyoxypropylene, polyoxypropylene-polyoxyethylene alcohols or mixtures thereof.

6. A process as claimed in claim 1, wherein the inert organic solvent used in preparing the mixtures of diphenylmethane diisocyanates and polyphenylpolymethylene polyisocyanates is monochlorobenzene, a dichlorobenzene or a mixture thereof and the monohydric or polyhydric polyoxyalkylene alcohols (ii) used are at least partially soluble in these solvents.

7. A process as claimed in claim 1, wherein the mixture of diphenylmethane diisocyanates and polyphenylpolymethylene polyisocyanates containing water and at least one monohydric and/or polyhydric polyoxyalkylene alcohol (ii) has incorporated into it, after the removal of the phosgene and the inert organic solvent and before the thermal treatment of the reaction product, at least one antioxidant based on phenol in an amount of at most 5% by weight and/or at least one aryl phosphite in an amount of at most 5% by weight, in each case based on the weight of the mixture of diphenylmethane diisocyanates and polyphenylpolymethylene polyisocyanates.

8. A process as claimed in claim 1, wherein the reaction mixture has incorporated into it, after phosgenation is complete and excess phosgene has been removed, a mixture of from more than 0.01 to less than 0.1% by weight of water (i) and from 0.05 to 5% by weight of at least one polyoxyalkylene alcohol (ii) having a functionality of from 2 to 3 and a hydroxyl number of from 200 to 800, based on the weight of the mixture of diphenylmethane diisocyanates and polyphenylpolymethylene polyisocyanates in the reaction mixture, the remaining phosgene still present and the inert organic solvent are then distilled off, the reaction mixture has added to it from 0 to 5% by weight of di-tert-butyl-p-cresol and/or triphenyl phosphite, based on the weight of the mixture of diphenylmethane diisocyanates and polyphenylpolymethylene polyisocyanates, and the reaction product is then thermally treated.

9. A process as claimed in claim 2, wherein the polyhydric polyoxyalkylene alcohols (ii) have a functionality of from 2 to 3 and a hydroxyl number of from 200 to 800.

10. A process as claimed in claim 2, wherein the monohydric or polyhydric polyoxyalkylene alcohols (ii) are selected from the group consisting of polyoxyethylene, polyoxypropylene, polyoxypropylene-polyoxyethylene alcohols or mixtures thereof.

11. A process for preparing a storage-stable mixture of diphenylmethane diisocyanate and polyphenylpolymethylene polyisocyanate including the steps of
   phosgenating raw MDA in the presence of an inert organic solvent to form a reactions mixture;
   adding to said reaction mixture water and an alcohol selected frog the group consisting of monohydric polyoxyalkylene alcohol, polyhydric polyoxyalkylene alcohol and mixtures thereof;
   allowing the resulting mixture reaction time;
   removing at least some excess phosgene from said resulting mixture; and
   removing at least some inert organic solvent from said resulting mixture.

12. The process as claimed in claim 11, wherein said step of phosgenating occurs in a temperature range of from 90 to 220 degrees C.

13. The process as claimed in claim 11, wherein said step of phosgenating occurs in a temperature range of from 120 to 180 degrees C.

14. The process as claimed in claim 11, wherein said step of phosgenating occurs in a pressure range of from I bar to 10 bars.

15. The process as claimed in claim 11, wherein said step of phosgenating occurs in a pressure range of from 2 to 5 bars.

16. The process as claimed in claim 11, wherein said reaction mixture contains at least one inert organic solvent, dissolved raw MDI, excess phosgene, and hydrogen chloride.

17. The process as claimed in claim 11, including the step of removing substantially all of the excess phosgene following completion of phosgenation and before water and said alcohol are added.

18. The process as claimed in claim 11, wherein said reaction time is between 2 and 25 minutes.

19. A process for preparing a storage-stable mixture of diphenylmethane diisocyanate and polyphenylpolymethylene polyisocyanate including the steps of forming a reaction mixture containing an inert organic solvent, phosgene, and raw MDI;

adding to said reaction mixture water and polyoxypropylene glycol to form a modified reaction mixture;

heating said modified reaction mixture; and dechlorinating said modified reaction mixture.

* * * * *